United States Patent [19]

Ochi et al.

[11] 4,225,524
[45] Sep. 30, 1980

[54] STEROID DERIVATIVES AND PROCESS FOR PREPARING THE SAME

[75] Inventors: Kiyoshige Ochi, Kawagoe; Isao Matsunaga; Minoru Shindo, both of Tokyo; Chikara Kaneko, Kanazawa, all of Japan

[73] Assignee: Chugai Seiyaku Kabushiki Kaisha, Tokyo, Japan

[21] Appl. No.: 915,988

[22] Filed: Jun. 14, 1978

[30] Foreign Application Priority Data

Jun. 24, 1977 [JP] Japan .................................. 52-74526
Aug. 24, 1977 [JP] Japan ................................. 52-100591

[51] Int. Cl.³ .................................................. C07J 9/00
[52] U.S. Cl. ................................. 260/397.2; 260/397.1
[58] Field of Search ...................................... 260/397.2; /Steroids MS File

[56] References Cited

U.S. PATENT DOCUMENTS

| | | | |
|---|---|---|---|
| 3,846,455 | 11/1974 | Ikekawa et al. | 260/397.3 |
| 3,868,396 | 2/1975 | Ikekawa et al. | 260/397.2 |
| 3,936,478 | 2/1976 | Takeshita et al. | 260/397.2 |

FOREIGN PATENT DOCUMENTS 50-149662  4/1975  Japan ...................................... 260/397.2

*Primary Examiner*—Elbert L. Roberts
*Attorney, Agent, or Firm*—Browdy and Neimark

[57] ABSTRACT

Steroid derivatives represented by the formula

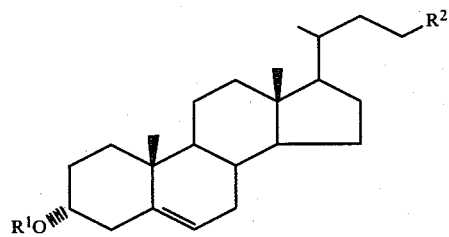

wherein $R^1$ and $R^2$ are as defined hereunder which is useful for easily producing a wide variety of active vitamin D, and a process for preparing the same are disclosed.

19 Claims, No Drawings

STEROID DERIVATIVES AND PROCESS FOR PREPARING THE SAME

This invention relates to a steroid derivative represented by the formula

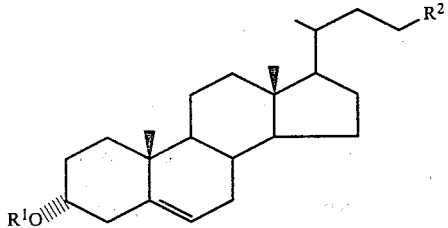

wherein $R^1$ is hydrogen or a protecting group for hydroxyl radical and $R^2$ is

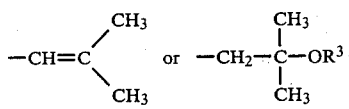

wherein $R^3$ is hydrogen or a protecting group for hydroxyl radical, and a process for preparing the same.

In recent years, extensive research has been carried on for developing active metabolites of vitamin D. Especially, steroid compounds having hydroxyl group attached to their side chain or steroid compounds into the side chain of which hydroxyl group can be easily introduced have attracted researchers' attention as an intermediate for the production of active vitamin $D_3$, for example, $1\alpha,25$-dihydroxycholecalciferol, $1\alpha,24,25$-trihydroxycholecalciferol, 25-hydroxycholecalciferol, 24,25-dihydroxycholecalciferol or the like.

Desmosterol is known as a useful intermediate for preparing the above active vitamin $D_3$. In fact, various types of active vitamin $D_3$ are derived from desmosterol. Although desmosterol is very useful as an intermediate for preparing the active vitamin $D_3$, it is difficult to obtain commercially as raw material because, for example, it is derived from fucosterol extracted from certain seaweeds, which is hardly available as natural substance.

After careful searching for ways to produce desired starting substances for an active vitamin D and, after intensive research it has been, found in accordance with the present invention that hyodeoxycholic acid, which is easily available, can be used to prepare the compound represented by the formula (I) with several reaction steps. Further, it has been found in accordance with the invention that an active vitamin D may be easily prepared using the compound (I) above.

The object compounds (I) of this invention are prepared by one of the following methods.

Among the object compounds (I), the compounds (I-a) in which $R^2$ in the formula (I) is

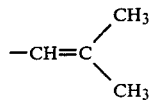

are prepared by dehydrating a compound represented by the formula

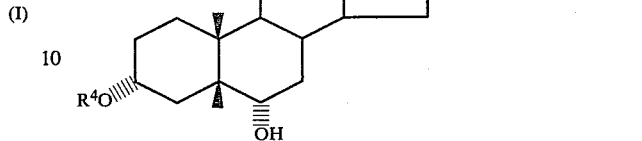

wherein $R^4$ is a protecting group for hydroxyl radical with aid of an acid catalyst to give the compound (III) represented by the formula

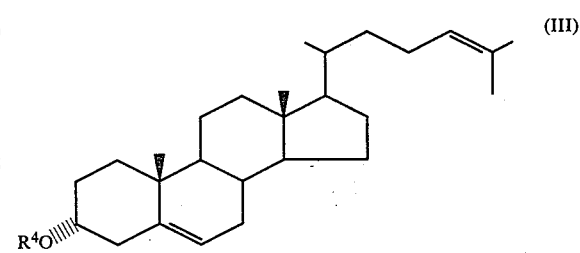

wherein $R^4$ is as defined above and, optionally, hydrolyzing the product to remove the protecting group.

Alternatively, the compounds (I-a) are also prepared by reacting the compound represented by the formula (II) with methanesulfonyl chloride or p-toluenesulfonyl chloride, heating the product to subject it to eliminating reaction to give the compound (III) and, optionally, hydrolyzing the product.

The compound (III) is reacted with a mercuric salt and then reduced with aid of an alkali metal borohydride and, if necessary, hydrolyzed to give the compounds (I-b) represented by the formula (I) wherein $R^2$ is

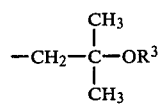

in which $R^3$ is as defined above.

The compounds (II) which are used as starting compounds may be prepared from hyodeoxycholic acid by, for example, a series of reactions represented by the following scheme.

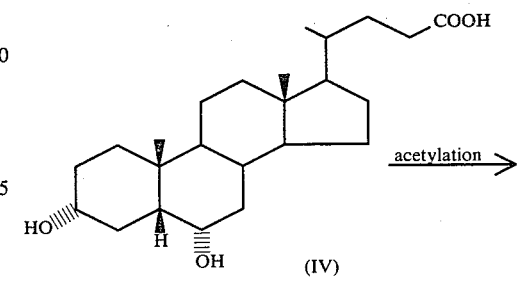

-continued

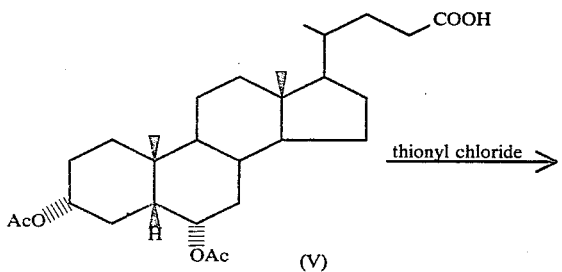

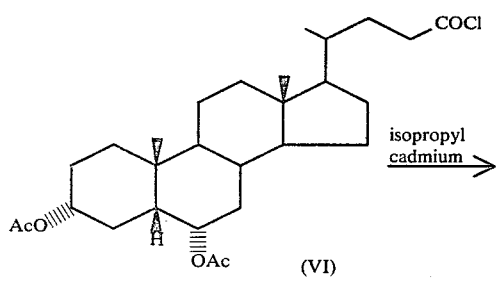

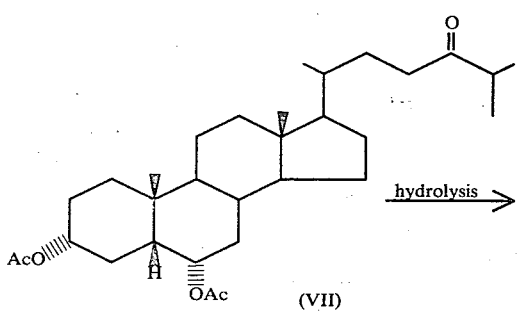

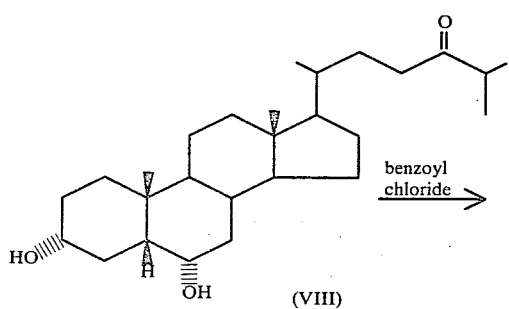

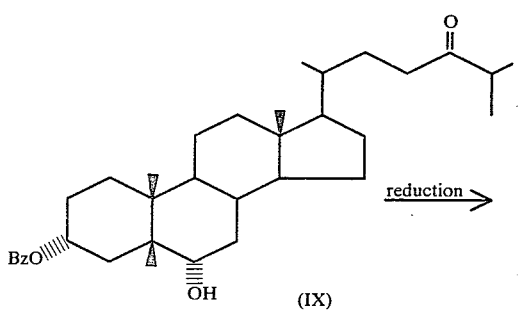

-continued

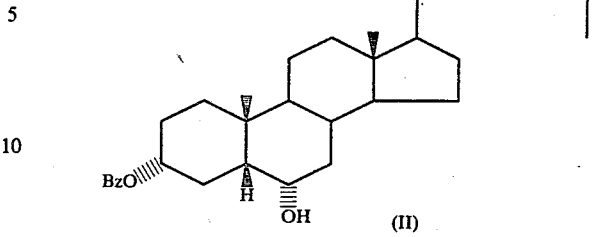

In the reaction scheme above, acetylhyodeoxycholic acid (V) is prepared by acetylating hyodeoxycholic acid (IV) in a conventional manner, and the compound (V) is reacted with thionyl chloride, phosphorus pentachloride or a like halogenating agent under heating in the presence of or in the absence of a solvent such as benzene, chloroform, etc. The compound (VI) is then reacted with an organometallic compound such as an isopropyl magnesium halide, an isopropyl zinc halide, diisopropyl cadmium or diisopropyl zinc in an inert solvent such as benzene, toluene, diethyl ether, etc., preferably, reacted with isopropyl cadmium in benzene, to give a compound (VII). The compound (VII) is hydrolyzed in a conventional manner to give the compound (VIII) which is then acylated in a conventional manner, for example, by reacting it with an acyl halide in the presence of a base such as pyridine to give the compound (IX). In this acylation reaction, undesired products such as a compound acylated at 6-hydroxyl radical and a compound acylated at 3- and 6-hydroxyl radicals will be produced. However, such undesired products can be hydrolyzed to return to the compound (VIII) which is then brought back to the acylation reaction.

In order to lower the yield of the byproducts, acylation is preferably effected with the minimum amount of an acylating agent at a low temperature.

The compound (IX) is then reduced, for example, with the aid of an alkali metal hydride to derive the compound (II) which is a starting compound of this invention. The reduction reaction may be effected with the use of an alkali hydride, for example, an alkali borohydride such as calcium borohydride, potassium borohydride or sodium borohydride; or lithium aluminium hydride. For the reduction reaction, a solvent such as an ether or an alcohol is preferably used.

In case $R^1$ and/or $R^2$ in the formula (I) representing the object compound of this invention are protecting group(s) for hydroxyl radicals, a protecting group such as acyl, triarylmethyl, methoxymethyl, tetrahydropyranyl, alkylsilyl or benzyl is preferred.

In the practice of the process of this invention, the following conditions may be used.

In the process for preparing the compound (I-a) from the compound (II) by dehydration with the use of an acid catalyst, the dehydration may be carried out by dissolving the compound (II) in a solvent such as benzene, chloroform, dichloromethane, dioxane or pyridine and adding an acid catalyst to the solution and allowing the mixture to react at a temperature of from 0° C. to reflux temperature of the solvent used for 10 minutes–24 hours. The acid catalysts which are useful in this invention include, for example, phosphorus oxychloride; thionyl chloride; methanesulfonic acid and p-toluenesulfonic acid or acid chloride thereof; phosphoric anhydride and sulfuric acid. In case phosphorus oxychloride, thionyl chloride, methanesulfonyl chloride or p-toluenesulfonyl chloride is used as an acid catalyst, the reaction may be preferably carried out for several hours in the presence of a tertiary amine such as pyridine, triethyl amine or dimethylaniline.

The process for producing the compound (I-a) by reacting the compound (II) with methanesulfonyl chloride or p-toluenesulfonyl chloride and eliminating the resulting mesylate or tosylate is carried out as follows. The first reaction may be carried out by dissolving the compound (II) in pyridine, triethylamine, dimethylformamide, ethyl acetate or benzene, adding methanesulfonyl chloride or p-toluenesulfonyl chloride to the solution, subjecting the mixture to reaction at a temperature of from 0° to 100° C., preferably 20° to 40° C. for 5-50 hours, preferably 15-25 hours. The eliminating reaction may be carried out by refluxing for 2-30 hours the mesylate or tosylate of the compound (II) in a solvent such as dimethylformamide, benzene or ethyl acetate. In order to perform the reaction smoothly, it is preferably carried out in the presence of an alkali metal halide such as lithium chloride, potassium chloride, lithium bromide or the like, or a tertiary amine such as triethylamine, pyridine, dimethyl aniline or the like.

The process for converting the compound (III) to the compound (I-b) is carried out as follows. The reaction introducing mercury oxyl group may be preferably carried out by dissolving the compound (III) in a mixed solvent of water and an organic solvent, adding to the solution a mercuric salt such as mercuric trifluoroacetate, mercuric acetate, mercuric bromide, mercuric chloride or the like and letting the mixture react at a temperature of from 0° to 50° C., preferably 20° to 30° C. for 5-10 hours. An organic solvent to be mixed with water includes, for example, tetrahydrofuran, dimethylformamide, dioxane or the like. The thus obtained mercury oxy compound may be reduced in situ with the aid of an alkali metal borohydride. The reduction reaction is effected by first alkalizing the reaction system with addition of sodium hydroxide or potassium hydroxide, adding the alkali metal borohydride such as sodium borohydride or potassium borohydride and subjecting the system to reaction at a temperature of from 0° to 20° C., for one hour to give the compound (I-b).

An example of process for preparation of $1\alpha,25$-dihydroxycholecalciferol as an active vitamin D from the compound of this invention is shown hereunder.

The compound (I-b) is hydrolyzed in a conventional manner if it has a protecting group for 3-hydroxyl, and reacted with 2,3-dichloro-5,6-dicyanobenzoquinone in an inert solvent to give 25-hydroxycholest-1,4,6-trien-3-one (X). Although any inert solvent which provides no adverse effect to the reaction may be used, aromatic solvents such as benzene and toluene, and ethers such as dioxane are preferably used. The desired results may be obtained if the molar ratio of 2,3-dichloro-5,6-dicyanobenzoquinone to the compound (III) ranges from 3:1 to 5:1. The reaction may be preferably carried out under heating.

The compound (X) may be easily converted to $1\alpha,25$-dihydroxycholecalciferol, for example, by a process described in Japanese Patent Disclosure No. 100056/75.

This invention is further illustrated by the following Examples.

EXAMPLE 1

The solution of hyodeoxycholic acid (30 g) in acetic anhydride (90 ml) and glacial acetic acid (180 ml) was refluxed for one hour. After cooling, the reaction mixture was evaporated and the residue was dissolved in pyridine (200 ml) and water (40 ml). The mixture as refluxed for one hour and then evaporated. The residue was dissolved in chloroform, and the chloroform layer was washed with water and a diluted aqueous hydrochloric acid, and dried over magnesium sulfate. Chloroform was evaporated to give 31 g of hyodeoxycholic acid diacetate.

IR spectrum (cm$^{-1}$, KBr): 1735, 1708. NMR spectrum ($\delta$ in CDCl$_3$): 0.65 (3H,S), 0.98 (6H,S), 2.01 (3H,S), 2.03 (3H,S), 4.4-5.4 (1H,m).

EXAMPLE 2

To the suspension of metallic magnesium flakes (4.46 g) in dry diethyl ether (200 ml) was added dropwise a solution of isopropyl bromide (18.9 ml) in dry diethyl ether (100 ml) while stirring at room temperature. The mixture was refluxed for 30 minutes to completely dissolve the magnesium flakes. After cooling, anhydrous cadmium bromide (25 g) was slowly added to the solution of isopropyl magnesium bromide and the mixture was refluxed for one hour. Then, most of diethyl ether was evaporated, and dry benzene was added to the residue to give a solution of diisopropyl cadmium in benzene.

Separately, acetylhyodeoxycholic acid (10 g) was dissolved in thionyl chloride (50 ml) and mildly heated for 30 minutes. After removal of excess thionyl chloride by evaporation under reduced pressure, the resulting diacetylhyodeoxycholic acid chloride was dissolved in dry benzene. The solution was added dropwise to the separately prepared solution of diisopropyl cadmium in benzene while vigorously stirring and then cooling with water. One hour after completion of the addition, water was added to the reaction mixture under cooling with ice-water and then a 5% aqueous solution of hydrochloric acid was added to decompose the excess reagent. The benzene layer was washed with water, dried over magnesium sulfate and evaporated to give an oily product, $3\alpha,6\alpha$-dihydroxy-$5\beta$-cholestan-24-one diacetate which had a melting point of 108°-109° C. after recrystallization from methanol.

IR spectrum (cm$^{-1}$, KBr): 1730, 1712. NMR spectrum ($\delta$ in CDCl$_3$): 0.66 (3H,S), 0.99 (6H,S), 1.10 (3H,S), 1.94 (6H,S), 4.3-4.8 (1H,m)

EXAMPLE 3

$3\alpha,6\alpha$-Dihydroxy-$5\beta$-cholestan-24-one diacetate prepared in Example 2 was dissolved in a solution of potassium hydroxide (11 g) in methanol (200 ml), and the solution was stirred at room temperature for 3 hours. The reaction mixture was concentrated into about 50 ml in volume. Water was added to the concentrate and the separated oil was extracted with ethyl acetate. The ethyl acetate layer was washed with water, dried over magnesium sulfate and evaporated. The residue was purified by chromatography on silica gel. Elution with chloroform gave 3 g of $3\alpha,6\alpha$-dihydroxy-$5\beta$-cholestan-24-one having a melting point of 180°-181° C. after recrystallization from ethyl acetate.

IR spectrum (cm$^{-1}$, KBr): 3360, 1710. NMR spectrum ($\delta$ in CDCl$_3$): 0.64 (3H, S), 0.90 (6H,S), 1.02 (3H, S), 1.14 (3H,S), 3.30-3.80 (2H,m), 3.80-4.40 (2H,m).

EXAMPLE 4

To a solution of 3α,6α-dihydroxy-5β-cholestan-24-one (2 g) in dichloromethane (30 ml) and pyridine (1 ml) was added benzoyl chloride (1 ml) under cooling with ice-water. Six hours after the addition, the reaction mixture was washed with a diluted aqueous hydrochloric acid and then with water, dried over magnesium sulfate and evaporated. The residue was chromatographed on silica gel (60 g) and eluted with chloroform. First, 3α,6α-dihydroxy-5β-cholestan-24-one dibenzoate (0.1 g) was eluted and then 3α,6α-dihydroxy-5β-cholestan-24-one 6-O-benzoate (0.6 g), and 3α,6α-dihydroxy-5β-cholestan-24-one 3-O-benzoate (0.4 g) were eluted in the order. Finally, elution with ethyl acetate gave unreacted starting compound (0.7 g).

Assay of 3α,6α-dihydroxy-5β-cholestan-24-one 3-O-benzoate showed as follows:

IR spectrum (cm$^{-1}$, KBr): 3450, 1712. NMR spectrum (δ in CCl$_4$): 0.60 (3H,S), 0.89 (3H,S), 0.99 (3H,S), 1.10 (3H,S), 4.00 (1H,m), 4.90 (1H,m), 8.00 (2H,m), 7.40 (3H,b.S).

EXAMPLE 5

A solution of 3α,6α-dihydroxy-5β-cholestan-24-one 3-O-benzoate (486.7 mg) in diethyl ether (5 ml) was added dropwise to a solution of calcium borohydride in methanol at $-10°$ C. which had been prepared from sodium borohydride (352 mg) and calcium chloride (672 mg). The mixture was stirred for 30 minutes at that temperature, neutralized with aqueous acetic acid and extracted with diethyl ether. The ether layer was washed with water, dried over magnesium sulfate and evaporated to give 471 mg of 3α,6α,24-trihydroxy-5β-cholestane 3-O-benzoate.

NMR spectrum (δ in CCl$_4$): 0.62 (3H,S), 0.82 (3H,S), 0.91 (6H,S), 3.0–4.2 (6H,m), 8.03 (2H,m), 7.4 (3H,m).

EXAMPLE 6

To a solution of 3α,6α,24-trihydroxy-5β-cholestane 3-O-benzoate (471 mg) was added phosphorus oxychloride (0.6 ml) and the mixture was refluxed for 15 minutes. After cooling, the reaction mixture was poured into ice-water and extracted with diethyl ether. The ether layer was washed with diluted aqueous hydrochloric acid and then with water, dried over magnesium sulfate and evaporated. The residue was chromatographed on silica gel (30 g) and eluted with chloroform to give 212.4 mg of epidesmosterol benzoate.

NHM spectrum (δ in CCl$_4$): 0.70 (3H,S), 1.04 (6H,b.S), 1.59 (3H,S), 1.66 (3H,S), 3.65 (1H,m), 4.85–5.60 (2H,m), 8.00 (2H,m), 7.45 (3H,m).

Epidesmosterol benzoate was hydrolyzed in a conventional manner using methanolic potassium hydroxide to give epidesmosterol which had a melting point of 137°–139° C. after recrystallization from methanol.

NMR spectrum (δ in CDCl$_3$): 0.69 (3H,S), 1.01 (6H,b.S), 1.61 (3H,S), 1.68 (3H,S), 4.00 (1H,m), 4.9–5.6 (2H,m).

Epidesmosterol was acetylated in a conventional manner with the use of acetic anhydride-pyridine to give epidesmosterol acetate having a melting point of 112°–115° C. after recrystallization from methanol.

IR spectrum (cm$^{-1}$, KBr): 1735. NMR spectrum (δ in CDCl$_3$): 0.69 (3H,S), 0.90 (3H,S), 1.01 (3H,S), 1.60 (3H,S), 1.69 (3H,S), 2.01 (3H,S), 4.9–5.6 (2H,m). mass spectrum (m/e): 384 (M$^+$), 369, 366, 351.

EXAMPLE 7

To a solution of epidesmosterol acetate (53 mg) in a mixture of tetrahydrofuran (1 ml) and dimethylformamide (1 ml) were added water (0.5 ml) and mercuric trifluoroacetate (0.1 g) followed by stirring at room temperature for 7 hours. To the reaction mixture were added 3 N aqueous sodium hydroxide (0.5 ml) and sodium borohydride (50 mg) and stirred at room temperature for one hour. The reaction mixture was extracted with ethyl acetate and the ethyl acetate layer was washed with water, dried over magnesium sulfate and evaporated. The residue was chromatographed on silica gel and eluted with chloroform to give 19 mg of 25-hydroxyepicholesterol acetate.

NMR spectrum (δ in CDCl$_3$): 0.68 (3H,S), 1.01 (3H,S), 1.20 (6H,S), 2.01 (3H,S), 5.01 (1H,m), 5.30 (1H,m).

25-Hydroxy-epicholesterol acetate was hydrolyzed in a conventional manner using methanolic potassium hydroxide to give 25-hydroxy-epicholesterol having a melting point of 157°–160° C. after recrystallization from methanol.

NMR spectrum (δ in CDCl$_3$): 0.68 (3H,S), 1.01 (3H,S), 1.20 (6H,S), 3.99 (1H,m), 5.42 (1H,m). mass spectrum (m/e): 402 (M$^+$), 384, 369, 351, 59.

EXAMPLE 8

To a solution of 25-hydroxy-epicholesterol (10 mg) in dioxane (2 ml) was added 2,3-dichloro-5,6-dicyanobenzoquinone (19.7 mg) and the mixture was refluxed for 16 hours. After cooling, precipitated 2,3-dichloro-5,6-dicyanohydroquinone was removed by filtration, and the filtrate was evaporated. The residue was chromatographed on alumina (5 g) and eluted with chloroform to give 4.5 mg of 25-hydroxycholest-1,4,6-trien-3-one having a melting point of 183°–184° C.

UV spectrum $\lambda_{max}^{EtOH}$ (nm): 223, 255, 299. IR spectrum (cm$^{-1}$, KBr): 3500, 1650.

The product was identified with the authentic sample by mixed melting point determination.

What is claimed is:

1. A process for preparing a steroid derivative represented by the formula

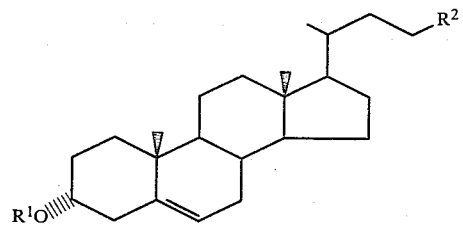

wherein R$^1$ is hydrogen or a protecting group for hydroxyl radical and R$^2$ is

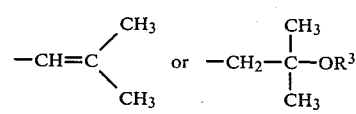

in which R$^3$ is hydrogen or a protecting group for hydroxyl radical, which comprises a method selected from the class consisting of:

(1) reacting a compound represented by the formula

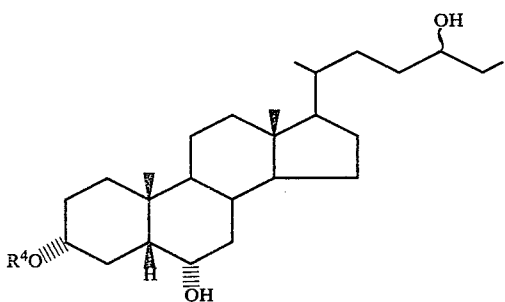

(II)

wherein $R^4$ is a protecting group for hydroxy radical, with an acid selected from the group consisting of phosphorus oxychloride, thionyl chloride, methane sulfonic acid, p-toluenesulfonic acid, methane sulfonylchloride, p-toluenesulfonyl chloride, phosphoric anhydride and sulfuric acid; and, optionally, hydrolyzing the product;

(2) reacting a compound represented by the formula

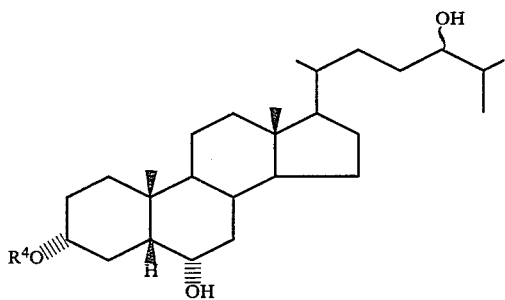

(II)

wherein $R^4$ is as defined above, with methanesulfonyl chloride or p-toluenesulfonyl chloride, heating the product to subject it to eliminating reaction and, optionally, hydrolyzing the product; or (3) reacting a compound represented by the formula

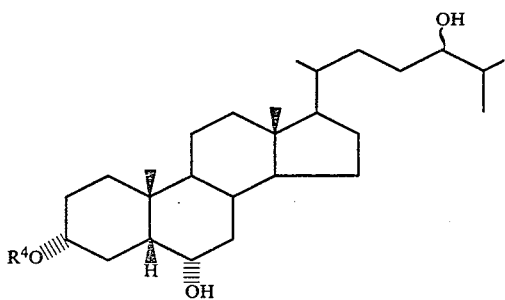

(II)

wherein $R^4$ is as defined above, with an acid selected from the group consisting of phosphorus oxychloride, thionyl chloride, methane sulfonic acid, p-toluenesulfonic acid, methane sulfonylchloride, p-toluenesulfonyl chloride, phosphoric anhydride and sulfuric acid; reacting the resulting compound represented by the formula

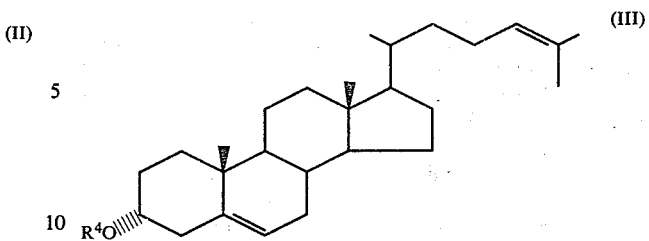

(III)

wherein $R^4$ is as defined above with a mercuric salt, reducing the resulting compound with an alkali metal borohydride and, optionally, hydrolyzing the product.

2. A process according to claim 1, wherein said acid catalyst in said method (1) is selected from the class consisting of phosphorus oxychloride, thionyl chloride, methanesulfonic acid, p-toluenesulfonic acid, methanesulfonyl chloride, p-toluenesulfonyl chloride, phosphoric anhydride and sulfuric acid.

3. A process according to claim 2 wherein said acid catalyst is selected from the class consisting of phosphorus oxychloride, thionyl chloride, methanesulfonyl chloride and p-toluenesulfonyl chloride.

4. A process according to claim 1 wherein said method (1) is carried out in an organic solvent.

5. A process according to claim 4 wherein said solvent is selected from the class consisting of benzene, chloroform, dichloromethane, dioxane and pyridine.

6. A process according to claim 1 wherein said reaction of the method (1) is carried out at a temperature ranging from 0° C. to the reflux temperature for 10 minutes–24 hours.

7. A process according to claim 3 wherein said reaction is carried out in the presence of an amine selected from the class consisting of pyridine, triethylamine and dimethylaniline for several hours.

8. A process according to claim 1 wherein the first reaction of the method (2) is carried out in a solvent selected from the class consisting of pyridine, triethylamine, dimethylformamide, ethyl acetate and benzene.

9. A process according to claim 1 wherein the first reaction of the method (2) is carried out at a temperature ranging from 0° to 100° C. for 5–50 hours.

10. A process according to claim 9 wherein said reaction is carried out at a temperature ranging from 20°–40° C. for 15–25 hours.

11. A process according to claim 1 wherein said eliminating reaction of the method (2) is carried out in a solvent selected from the class consisting of dimethylformamide, benzene and ethyl acetate.

12. A process according to claim 1 wherein said eliminating reaction of the method (2) is carried out by refluxing for 2–30 hours.

13. A process according to claim 1 wherein said eliminating reaction of the method (2) is carried out in the presence of an alkali halide selected from the class consisting of lithium chloride, potassium chloride and lithium bromide or a tertiary amine selected from the class consisting of triethylamine, pyridine and dimethylaniline.

14. A process according to claim 1 wherein said reaction of the compound (III) with the mercuric salt in the method (3) is carried out in a mixed solvent of water with an organic solvent selected from the class consisting of tetrahydrofuran, dimethylformamide and dioxane.

15. A process according to claim 1 wherein said reaction of the compound (III) with the mercuric salt in the method (3) is carried out at a temperature ranging from 0° to 50° C. for 5-10 hours.

16. A process according to claim 15 wherein said reaction is carried out at a temperature ranging from 20° to 30° C.

17. A process according to claim 1 wherein said mercuric salt is selected from the class consisting of mercuric trifluoroacetate, mercuric acetate, mercuric bromide and mercuric chloride.

18. A process according to claim 1 wherein said reduction reaction of the method (3) is carried out at a temperature ranging from 0° to 20° C. for one hour.

19. A process according to claim 1 wherein said alkali metal borohydride used in the method (3) is selected from the class consisting of sodium borohydride and potassium borohydride.

* * * * *